United States Patent [19]

Winn et al.

[11] 3,946,111
[45] Mar. 23, 1976

[54] PHARMACEUTICAL COMPOSITIONS CONTAINING 1 OR 2-MONO AND DIALKYL SUBSTITUTED THIENOBENZOPYRANS AND PHARMACOLOGICAL USES THEREOF

[75] Inventors: Martin Winn, Deerfield, Ill.; Raj Kumar Razdan, Belmont; Haldean Cloyce Dalzell, Weston, both of Mass.; Joyce Ruth Krei, Glenview, Ill.

[73] Assignee: Sharps Associates, Cambridge, Mass.

[22] Filed: Nov. 18, 1974

[21] Appl. No.: 524,626

Related U.S. Application Data

[62] Division of Ser. No. 392,636, Aug. 29, 1973, Pat. No. 3,895,034.

[52] U.S. Cl. .................................................. 424/275
[51] Int. Cl.² ......................................... A61K 31/38
[58] Field of Search ................................... 424/275

[56] References Cited
UNITED STATES PATENTS

| | | | |
|---|---|---|---|
| 3,639,426 | 2/1972 | Razdan | 260/343.2 R |
| 3,639,427 | 2/1972 | Razdan | 260/345.3 |
| 3,656,906 | 4/1972 | Bullock | 23/230 B |
| 3,801,597 | 4/1974 | Makisumi | 260/332.2 H |

*Primary Examiner*—Jerome D. Goldberg
*Attorney, Agent, or Firm*—Merriam, Marshall, Shapiro & Klose

[57] ABSTRACT

1,2-Dihydro-4H-thieno-[2,3-c][1]benzopyrans of the formulae

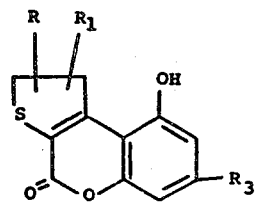

and

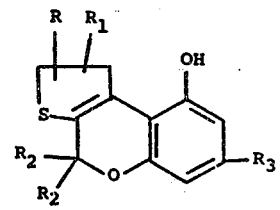

wherein R is a lower alkyl group having 1 to 5 carbons, $R_1$ is hydrogen or a lower alkyl group having 1 to 5 carbons, $R_2$ is a lower alkyl group and $R_3$ is an alkyl group having 1 to 20 carbon atoms, a phenyl-lower alkyl group or a cycloalkyl-lower alkyl group. The compounds have analgesic, antihypertensive, antidepressant, anticonvulsant, antianxiety, sedative-hypnotic and/or tranquilization activity.

2 Claims, No Drawings

PHARMACEUTICAL COMPOSITIONS CONTAINING 1 OR 2-MONO AND DIALKYL SUBSTITUTED THIENOBENZOPYRANS AND PHARMACOLOGICAL USES THEREOF

This application is a divisional of our copending application Ser. No. 392,636 filed Aug. 29, 1973 now U.S. Pat. No. 3,895,034.

This invention relates to novel chemical compounds and processes of producing the same. More particularly, this invention is concerned with novel 1,2-dihydro-4H-thieno[2,3-c][1] benzopyrans and the use of such compounds, particularly those having pharmacological activity.

According to one aspect of the subject invention there is provided novel 1,2-dihydro-4H-thieno[2,3-c][1] benzopyrans of the formula

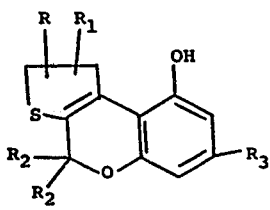

Formula 1 wherein R is a lower alkyl group having 1 to 5 carbon atoms and $R_1$ is hydrogen or a lower alkyl group having 1 to 5 carbon atoms, and when R and $R_1$ are both lower alkyl such groups can be on the same or different carbon atoms in the thieno ring, $R_2$ is a lower alkyl group and $R_3$ is an alkyl group having 1 to 20 carbon atoms, a phenyl-lower alkyl group or a cycloalkyl-lower alkyl group, and novel intermediates useful in making such compounds. When R and $R_1$ are both in the 1-position on the thieno ring, generally only one of such groups will be alkyl and the other will be hydrogen. The compounds where $R_3$ is an alkyl having 5 to 10 carbons are particularly useful as are the compounds when R, $R_1$ and $R_2$ are lower alkyl groups having 1 to 3 carbon atoms, and especially methyl.

As used herein, the term "lower-alkyl" means saturated, monovalent aliphatic-radicals, including straight and branched-chain radicals of from one to six carbon atoms, as illustrated by, but not limited to methyl, ethyl, propyl, isopropyl, butyl, sec.-butyl, amyl, hexyl and the like.

As used herein, the term "alkyl" means saturated, monovalent aliphatic radicals, including straight and branched chain radicals of from one to 20 carbon atoms, as illustrated by, but not limited to methyl, n-amyl, n-hexyl, 2-heptyl, n-heptyl, 3-methyl-2-octyl, n-octyl, 2-nonyl, 2-tetradecyl, n-hexadecyl, 2-eicosanyl, and the like.

As used herein, the term "cycloalkyl" means cyclic, saturated aliphatic-radicals of from three to eight carbon atoms, as illustrated by, but not limited to cyclopropyl, cyclobutyl, 2-methylcyclobutyl, cyclohexyl, 4-methylcyclohexyl cyclooctyl, and the like.

As used herein, the term "phenyl-lower alkyl", means a monovalent radical consisting of a phenyl nucleus bonded to the rest of the molecule, respectively, through a divalent lower-alkylene radical of from one to six carbon atoms as illustrated by, but not limited to methylene, 1,1-ethylene, 1,2-ethylene, 1,3-propylene, 1,2-propylene, 1,4-butylene, and the like. Here and elsewhere throughout this specification, it will be understood that the benzene or phenyl ring can bear any number and kind of substituents such as would occur to the person skilled in organic chemistry. Solely for illustration, and without limitation, such substituents include lower-alkyl, lower-alkoxy, halo (chloro, bromo, iodo or fluoro), nitro, lower-alkylmercapto, and the like.

The compounds of Formula 1 can be prepared by reacting a 5-substituted resorcinol of Formula 2

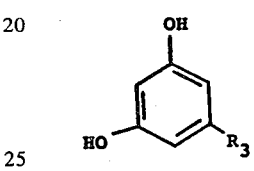

Formula 2 wherein $R_3$ has the previously assigned significance, with a 3-oxo-tetrahydrothiophene-2-carboxylate of Formula 3

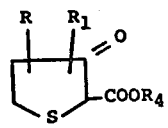

Formula 3 wherein $R_4$ represents a lower alkyl group, to produce a 1,2-dihydro-4-oxo-4H-thieno[2,3-c][1] benzopyran of Formula 4

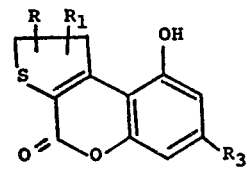

Formula 4 which can then be reacted with a lower alkyl magnesium halide to produce a compound of Formula 5

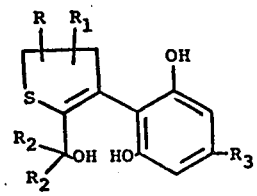

Formula 5 which is then reacted with an acid such as hydrochloric acid or p-toluene sulfonic acid to dehydrate it to produce a 4,4-dialkyl-1,2-dihydro-9-hydroxy-7-$R_3$4H-Thieno-[2,3-c][1] benzopyran of Formula 1, wherein in Formulas 2 to 5 the substituents and symbols have the meanings assigned as with respect to Formula 1.

Some of the 5-substituted resorcinols which can be used in the process are 5-(3-methyl-2-octyl)resorcinal, 5-n-pentylresorcinol, 5-benzylresorcinol. 5-(3-phenylpropyl)resorcinol, 5-[2-(p-fluorophenyl)ethyl] resorcinol, 5-cyclopentylmethyl resorcinol and 5-(3-cyclohexylporpyl) resorcinol. The resorcinol starting materials are disclosed in the chemical literature and many are commercially available.

The 3-oxo-tetrahydrothiophene-2-carboxylates, and others within the scope of Formula 3, which can be used in the invention can be produced by the known Dieckmann cyclization of a di-lower alkyl 4 or 5R$_1$ - 4 or 5 R$_2$-3-thiahexanedioate. This can be illustrated by the cyclization of dimetnyl 5-methyl-3-thiahexanedioate to methyl 4-methyl-3-oxo-tetrahydrothiophene-2-carboxylate according to the following reaction:

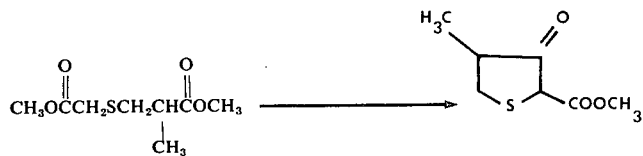

Some of the 3-oxo-tetrahydrothiophene-2-carboxylates of Formula 3 which can be prepared as described and used as starting materials are methyl4-methyl-3-oxo-tetrahydrothiophene-2-carboxylate, ethyl 5,5-dimethyl-3-oxo-tetrahydrothiophene-2-carboxylate, ethyl 5-methyl-3-oxo--tetrahydrothiophene-2-carboxylate, ethyl 5-propyl-3-oxo-tetrahydrothiophene-2-carboxylate and methyl 4-ethyl-3-oxo-tetrahydrothiophene-2-carboxylate.

The process in which the 5-substituted resorcinol is reacted with a 3-oxo-tetrahydrothiophene-2-carboxylate of Formula 3 to produce a compound of Formula 4 is readily effected by bringing the reactants together in a suitable liquid reaction medium in the presence of an acid catalyst. Hydrochloric acid dissolved in ethanol is suitable for conducting the reaction. The reaction can be carried out also in a mixture of concentrated sulfuric acid and phosphorous oxychloride, or in phosphorus oxychloride either alone or in an organic solvent, for example benzene or toluene. The product can be recovered from the reaction mixture by conventional means.

Some of the products produced by the described reaction which come within the scope of Formula 4 are 1,2-dihydro-9-hydroxy-1-methyl-7-(3-methyl-2-octyl)-4-oxo-4H-thieno[2,3-c][1]benzopyran, 1,2-dihydro-2,2-dimethyl-9-hydroxy-7-(3-methyl-2-octyl)-4-oxo-4H-thieno[2,3-c][1]-benzopyran, 1,2-dihydro-2,2-dimethyl-9-hydroxy-7-n-pentyl-4-oxo-4H-thieno-[2,3-c][1]benzopyran, 1,2-dihydro-9-hydroxy-2-methyl-7-[3-methyl-2-octyl]-4-oxo-4H-thieno[2,3-c][1]- benzopyran, 1,2-dihydro-9-hydroxy-2-methyl-7-n-pentyl-4-oxo-4H-thieno-[2,3-c][1]benzopyran, 1,2-dihydro-9-hydroxy-1-ethyl-7-(3-phenylpropyl)-4-oxo-4H-thieno-[2,3-c][1]benzopyran, and 1,2-dihydro-7-(3-cyclohexylpropyl)-9-hydroxy-2-propyl-4-oxo-4H-thieno[2,3-c][1]benzopyran.

The compounds of Formula 4 can be converted to the compounds of Formula 5 by reacting a compound of Formula 5 with an alkyl magnesium halide such as methyl magnesium chloride, ethyl magnesium iodide or propyl magnesium chloride. The reaction can be effected by bringing the reactants together in a suitable inert liquid reaction medium such as diethyl ether, dibutyl ether, tetrahydrofuran, anisole and pyridine. The reaction proceeds rapidly at reflux temperature. Although the desired product of Formula 5 can be isolated from the reaction mixture by standard methods after the reaction is terminated, it is generally not advantageous to isolate the triol. Instead, the triol of Formula 5 can be treated, without isolation, with an acid to convert it to a compound of Formula 1.

Some of the compounds of Formula 1 which can be produced as described are 1,2-dihydro-1,4,4-trimethyl9-hydroxy-7-(3-methyl-2-octyl)-4H-thieno-[2,3-c][1] benzopyran, 1,2-dihydro-9-hydroxy-7-(3-methyl-2-octyl)-2,2,4,4-tetramethyl-4H-thieno[2,3-c][1] benzopyran, 1,2-dihydro-9-hydroxy-2,2,4,4-tetramethyl-7-n-pentyl-4H-thieno-[2,3-c] [1] benzopyran, 1,2-dihydro-2,4,4-trimethyl-9-hydroxy-7-(3-methyl-2-octyl)-4H-thieno[2,3-c] [1] benzopyran, 1,2-dihydro 9-hydroxy-7-n-pentyl-2,4,4-trimethyl-4H-thieno [2,3-c][1]-benzopyran, 1,2-dihydro-9-hydroxy-7-(3-phenylpropyl)-1,4,4-triethyl-4H-thieno-[2,3-c][1] benzopyran, and 1,2-dihydro-7-(3-cyclohexylpropyl)-4,4-dimethyl-9-hydroxy-2-propyl-4-H-thieno [2,3-c][1] benzopyran.

The compounds of this invention have antihypertensive, antidepressant, analgesic, anticonvulsant and/or antianxiety activity in animals and such activities indicates potential human use for the compounds as drugs.

The pharmacological activity for the compounds having the nuclear alkyl substituents in the c-ring of this invention is surprisingly different from the activity of the prior art related compound 1,2-dihydro-4,4-dimethyl-9-hydroxy-7-(3-methyl-2-octyl)-4H-thieno-[2,3-c][1] benzopyran (SP-6) disclosed in Nature, Vol. 226, June 27, 1970, pp. 1265-67 which does not have an alkyl group in the c-ring. This will be seen from the following summaries of the pharmacological activity of SP-6 and specific compounds provided by this invention. The data reported in the summaries was obtained using test procedures reported in the literature as follows:

1. Antihypertensive test using hypertensive rats: Tabei et al., Clinical Pharmacology and Therapeutics, 11, No. 2, p. 269 (1970).

2. Mouse modified DOPA potentiation test for antidepressant activity: Everett, G.M., Proc. First Internat. Sympos. Antidepressant Drugs, Excerpta Med. Int. Cong. Ser. No. 122, 1966.

3. Audiogenic seizure test for anticonvulsant activity: Plotnikoff, N.P., J. Pharmacol. Exp. Therap. 119, 294 (1957).

4. Mouse fighting test for tranquilizing activity: Tedeschi, R. E. et al., J. Pharmacol. Exp. Therap., 125, 28 (1959) with modifications; response to footshock measured.

5. Acetic acid induced writhing test for analgesic activity: Brit. J. Pharmacol, 22, 296 (1964).

6. Rat tail flick test for analgesic activity: J. Pharmacol. Exper. Therap., 72, 74 (1941).

7. Hot plate test for analgesic activity: J. Pharmacol. Exper. Therap., 80, 300 (1944).

8. Sedative-hypnotic test: Jewett & Norton, Experimental Neurology, 15, 463-474 (1966), with modifications.

1,2-dihydro-4,4-dimethyl-9-hydroxy-7-(3-methyl-2-octyl)-4H-thieno-[2,3-c] [1] benzopyran (SP-6) administered orally in a dose of 10 mg./kg., reduced the systolic blood pressure of genetically hypertensive rats. At oral doses of 5, 10 and 20 mg./kg., it showed marked activity in the mouse modified DOPA potentiation test. In the audiogenic seizure test, SP-6 at oral doses of 10 and 30 mg./kg., protected 40% and 60% of the mice, respectively, from the convulsions. At an oral dose of 10 mg./kg., SP-6 caused a 67% reduction in fighting behavior in the mouse fighting test. SP-6 had very mild activity in the acetic acid induced writhing test in mice ($ED_{50} = 71.8$ mg./kg., p.o.). SP-6 at an oral dose of 1.0 mg./kg., caused an increase of 30 minutes in total sleep time in EEG sleep (sedative-hypnotic) studies in cats. This increase was a result of an increase of 49 minutes in the slow wave stage of sleep, a decrease of 19 minutes in the spindle stage, and no change in the rapid eye movement (REM) stage. At an oral dose of 2.0 mg./kg., SP-6 caused an increase of 31 minutes in total sleep time. This increase was a result of an increase of 70 minutes in the slow wave stage, a decrease of 40 minutes in the spindle stage, and an increase of 1 minute in the REM stage of sleep. SP-6 by these tests has antihypertensive, antidepressant, anticonvulsant, sedative-hypnotic and anti-anxiety or tranquilization activity.

1,2-dihydro-1,4,4-trimethyl-9-hydroxy-7-(3-methyl-2-octyl)-4H-thieno-[2,3-c][1] benzopyran (SP-147) administered orally in a dose of 10 mg./kg., reduced the systolic blood pressure of genetically hypertensive rats. At an oral dose of 10 mg./kg. it showed marked activity in the mouse modified DOPA potentiation test. In the audiogenic seizure test, SP-147 in oral doses of 10 and 30 mg./kg., protected 40% and 80% of the mice, respectively, from the convulsions. At an oral dose of 10 mg./kg., SP-147 caused a 62% reduction in fighting behavior in the mouse fighting test. SP-147 had very potent activity in the hot plate ($ED_{50} = 1.4$ mg./kg. p.o.), writhing ($ED_{50} = 4.7$ mg./kg., p.o.), and rat tail flick ($ED_{50} = 1.4$ mg./kg. p.o.) analgesic tests. SP-147 at an oral dose of 0.1 mg./kg., caused an increase of 21 minutes in total sleep time in EEG sleep (sedative-hypnotic) studies in cats. This increase was a result of an increase of 8 minutes in the slow wave stage of sleep, an increase of 19 minutes in the spindle stage, and an decrease of 6 minutes in the rapid eye movement (REM) stage of sleep. At an oral dose of 0.25 mg./kg., SP-147 caused an increase of 50 minutes in total sleep time. This increase was a result of an increase of 56 minutes in the slow wave stage, an increase of 2 minutes in the spindle stage, and a decrease of 8 minutes in the REM stage. At an oral dose of 0.5 mg./kg., SP-147 caused an increase of 108 minutes in total sleep time. This increase was a result of an increase of 61 minutes in the slow wave stage, a increase of 3 minutes in the spindle stage, and an increase of 44 minutes in the REM stage of sleep. Activity in these procedures show SP-147 useful as an antihypertensive, antidepressant, anticonvulsant, sedative-hypnotic and anti-anxiety agent and that it has pronounced analgesic activity.

1,2-dihydro-2,2-dimethyl-9-hydroxy-7-(3-methvl-2-octyl)-4-oxo-4H-thieno-[2,3-c][1] benzopyran SPA-16 administered orally in a dose of 10 mg./kg., showed no reduction in the systolic blood pressure of genetically hypertensive rats. At an oral dose of 20 mg./kg., it showed moderate activity in the mouse modified DOPA potentiation test. In the audiogenic seizure test, SPA-16 at an oral dose of 30 mg./kg., protected 20% of the mice from the convulsions. At an oral dose of 10 mg./kg., SPA-16 caused a 40% reduction in fighting behavior in the mouse fighting test. SPA-16 had no analgesic activity at the doses employed. Activity in these tests indicates SPA-16 is useful as an antidepressant agent.

1,2-dihydro-9-hydroxy-7-(3-methyl-2-octyl)-2,2,4,4-tetramechyl-4H-thieno-[2,3-c][l] benzopyran (SPA-19) administered orally in a dose of 10 mg./kg., showed no reduction in the systolic blood pressure of genetically hypertensive rats. In an oral dose of 20 mg./kg., it showed marked activity in the mouse modified DOPA potentiation test. In the audiogenic seizure test, SPA-19 in an oral dose of 30 mg./kg., protected 20% of the mice from the convulsions. At an oral dose of 10 mg./kg., SPA-19 caused a 36% reduction in fighting behavior in the mouse fighting test. SPA-19 had no analgesic activity at the doses employed. Activity in these tests indicates SPA-19 is useful as an antidepressant agent.

1,2-dihydro-2,2-dimethyl-9-hydroxy-7-n-pentyl-4-oxo-4H-thieno-[2,3-c] [1] benzopyran (SPA-24) administered orally in a dose of 10 mg./kg., showed no reduction in the systolic blood pressure of genetically hypertensive rats. In an oral dose of 5 mg./kg., it showed moderate activity in the mouse modified DOPA potentiation test. In the audiogenic seizure test, SPA-24 at an oral dose of 30 mg./kg., afforded no protection to the mice from the convulsions. At an oral dose of 10 mg./kg., SPA-24 caused a 28% reduction in fighting behavior in the mouse fighting test. SPA-24 had no analgesic activity at the doses employed. SPA-24 is useful as an antidepressant agent.

1,2-dihydro-9-hydroxy-2,2,4,4-tetramethyl-7-n-pentyl-4H-thieno-[2,3-c][1] benzopyran (SPA-38) administered orally in a dose of 10 mg./kg., showed no reduction in the systolic blood pressure of genetically hypertensive rats. At an oral dose of 20 mg./kg., it showed moderate activity in the mouse modified DOPA potentiation test. In the audiogenic seizure test, SPA-38 at an oral dose of 30 mg./kg., afforded no protection to the mice from the convulsions. At an oral dose of 10 mg./kg., SPA-38 caused a 36% reduction in fighting behavior in the mouse fighting test. SPA-38 had no analgesic activity at the doses employed. SPA 38 is useful as an antidepressant agent.

1,2-dihydro-9-hydroxy-2-methyl-7-n-pentyl-4-oxo 4H-thieno-[2,3-c][1] benzopyran (SPA-41) administered orally in a dose of 10 mg./kg., showed no reduction in the systolic blood pressure of genetically hypertensive rats. At an oral dose of 10 mg./kg., it showed moderate activity in the mouse modified DOPA potentiation test. In the audiogenic seizure test, SPA-41 in an oral dose of 30 mg./kg., afforded no protection to the mice from the convulsions. At an oral dose of 10 mg./kg., SPA-41 caused a 31% reduction in fighting behavior in the mouse fighting test. SPA-41 had no analgesic activity at the doses employed. SPA-41 is useful as an antidepressant agent.

1,2-dihydro-9-hydroxy-2-methyl-7-(3-methyl-2-octyl)-4-oxo-4H-thieno-[2,3-c][1] benzopyran (SPA-42) was not tested in genetically hypertensive rats. At an oral dose of 20 mg./kg., it showed only slight activity in the mouse modified DOPA potentiation test. In the audiogenic seizure test, SPA-42 in an oral dose of 30 mg./kg., afforded no protection to the mice from the convulsions. At an oral dose of 10 mg./kg., SPA-42 caused a 31% reduction in fighting behavior in the mouse fighting test. SPA-42 had no analgesic activity at the doses employed. SPA-42 is useful as a mild anti-anxiety agent (tranquilizer).

1,2-dihydro-2,4,4-trimethyl-9-hydroxy-7-(3-methyl2-octyl)-4H-thieno-[2,3-c][1] benzopyran (SPA-46) administered orally in a dose of 10 mg./kg., showed no reduction in the systolic blood pressure of genetically hypertensive rats. At an oral dose of 20 mg./kg., it showed marked activity in the mouse modified DOPA potentiation test. In the audiogenic seizure test, SPA-46 in oral doses of 10 and 30 mg./kg., protected 20% and 60% of the mice, respectively, from the convulsions. At an oral dose of 10 mg./kg., SPA-46 caused a 43% reduction in fighting behavior in the mouse fighting test. SPA-46 had moderate activity in the acetic acid induced writhing test in mice ($ED_{50} = 34$ mg./kg., p.o.). SPA-46 is useful as an antidepressant, anticonvulsant, or analgesic agent.

SUMMARY

SP-147 is approximately comparable in potency to SP-6 as both an anticonvulsant and an anti-anxiety agent. However, SP-147 is much more potent than SP-6 as a sedativehypnotic and analgesic agent, and is less potent than SP-6 as an antidepressant.

SPA-16, SPA-19, SPA-24, SPA-38 and SPA-41 are somewhat less potent than SP-6 as antidepressants, but the antihypertensive, anticonvulsant, anti-anxiety, and analgesic properties have been greatly reduced or lost altogether. These compounds thus have a much more selective activity than SP-6 thus indicating a usefulness where the broad spectrum of activities of SP-6 would be contra indicated. There do not appear to be large differences in potency among these five compounds (excluding SP-6) in the various tests.

The potency of SPA-42 is also selective to inducement of mild anti-anxiety activity.

SPA-46 is more potent as an analgesic agent than SP-6. SPA-46 is somewhat less potent than SP-6 as an antidepressant, and comparable in potency as an anticonvulsant.

The amount of active ingredient administered may be varied; however, it is necessary that the amount of active ingredient be such that a suitable dosage is given. The selected dosage depends upon the desired therapeutic effect, on the route of administration and on the duration of treatment. Dosages of from 0.1 to 25 mg./kg. of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one of more of the active compounds. Unit dosage forms, such as tablets and capsules, can contain about 2 to 300 mg. of active agent.

A typical tablet can have the composition:

|  | Mg |
|---|---|
| Active agent (1) | 100 |
| Starch U.S.P. | 57 |
| Lactose U.S.P. | 73 |
| Talc. U.S.P. | 9 |
| Stearic acid | 12 |

(1) 1,2-dihydro-1,4,4-trimethyl-9-hydroxy-7-(3-methyl-2-octyl)-4H-thieno-[2,3-c][1]benzopyran.

The compounds of Formula 1 exhibit both oral and parenteral activity and accordingly can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The following examples are presented to further illustrate the invention.

EXAMPLE 1

1,2-Dihydro-9-hydroxy-1-methyl-7-(3-methyl-2-octyl)-4-oxo4H-thieno-[2,3-c][1] benzopyran A. Dimethyl 5-methyl-3-thiahexanedioate

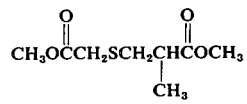

Methyl methacrylate (125 g.; 1.25 moles) was added dropwise during 30 min. to a stirred mixture of 127 g. (1.20 moles) of methyl mercaptoacetate and 1.0 ml. of piperidine and the temperature during addition was kept at about 45°C. by appropriate cooling. More piperidine (0.5 ml.) was added after 75 ml. of the acrylate had been introduced, and more (0.5 ml.) added after 115 ml. of the acrylate had been added. The reaction mixture was kept at 45°C. for 2 hr. longer and then it was allowed to cool. After standing overnight at room temperature, the mixture was diluted with about 50 ml. of methylene chloride, washed with 200 ml. of water, with 200 ml. of dilute hydrochloric acid and again with water. The solvent was removed and the residue was distilled to give the product as 227 g. (92%) of colorless liquid, b.p. 90°–92°C./0.7 mm.

B. Methyl 4-methyl-3-oxo-tetrahydrothiophene-2-carboxylate

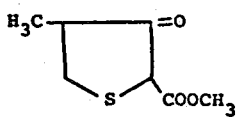

While a suspension of 35.4 g. (0.656 mole) of sodium methoxide in 1000 ml. of dry toluene was stirred vigorously, 112.6 g. (0.546 mole) of dimethyl 5-methyl-3-thiahexanedioate was added over a period of 70 min. The temperature of the reaction mixture was held at 85°–90°C. by heating in an oil bath. After the addition was completed, the bath temperature was raised to 105°C. while methanol was removed by distillation. The bath temperature was further increased and the distillation continued until the vapor temperature reached the boiling point of toluene. After the reaction solution had cooled overnight it was made acidic by the addition of dilute acetic acid. The toluene layer was washed with water, with saturated aqueous sodium chloride, and dried over sodium sulfate. Following removal of the solvent the residual orange liquid was distilled and the product collected as 73 g. (77%) of a pale yellow liquid, b.p. 75°–76°C./0.2 mm. The product is reported in Chem. Ab. 63, 5491 (1965).

C. 1,2-Dihydro-9-hydroxy-1-methyl-7-(3-methyl-2-octyl)-4-oxo-4H-thieno-[2,3-c][1] benzopyran

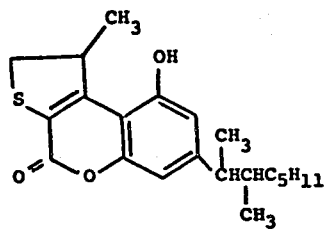

A solution in dry benzene of equimolar amounts of methyl 4-methyl-3-oxo-tetrahydrothiophene-2-carboxylate and 5-(3-methyl-2-octyl) resorcinol plus phosphorous oxychloride (5 ml. of benzene/g. of the resorcinol) was warmed for 13 days at 35°–37°C. in an oil bath. Most of the benzene and HCl were removed at reduced pressure, and the dark tarry residue was stirred with ether and water until solution was complete. The ether layer was washed successively with dilute solutions of sodium bicarbonate, sodium hydroxide and sodium carbonate, then with water and saturated sodium chloride. Drying and concentrating the final organic solution left a friable brick-red foamy solid.

The pyrone was recovered from this crude product by chromatography on a magnesium silicate column using 100% $CHCl_3$ and 1:99 $MeOH/CHCl_3$ solvent systems. Fractions containing the desired material (tlc) were concentrated to dryness and caused to solidify by standing under petroleum ether. The compound was further purified to give a yellow solid, m.p. 105°–107°C., (41% yield).

EXAMPLE 2

1,2-Dihydro-1,4,4-trimethyl-9-hydroxy-7-(3-methyl-2-octyl)-4H-thieno-[2,3-c][1] benzopyran

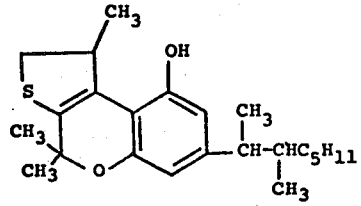

A solution of 4.6 g. (0.0128 mole) of 1,2-dihydro-9-hydroxy-1-methyl-7-(3-methyl-2-octyl)-4-oxo-4H-thieno[2,3-c][1]-benzopyran in 140 ml. of anhydrous diethyl ether was added during 30 min. with stirring to a solution of methylmagnesium bromide in 140 ml. of anhydrous ether, prepared from 3.7 g. (0.154 mole) of magnesium shavings by bubbling in methyl bromide until the solid metal had dissolved. After 15 min. of additional stirring at room temperature, the reaction mixture was heated at reflux for 1.5 hr.

The excess Grignard reagent was decomposed by the addition of a saturated solution of ammonium sulfate followed by additional water and dilute hydrochloric acid. The organic layer was separated, washed to neutrality with water, dried, and evaporated in a rotary evaporator. The residue was dissolved in 30 ml. of warm methanol and was dehydrated by the addition of 2 drops of concentrated hydrochloric acid and warming. The reaction mixture was added to water and the product was extracted into ethyl ether. The ether solution was washed free of acid, dried, and concentrated in a rotary evaporator, leaving 5.2 g. of a brown oil.

The oil was purified by column chromatography (silica gel, graded ethyl ether/petroleum ether), yielding 4.3 g. (90%) of product as a cloudy, pale yellow oil from the fractions eluted by 1:99 and 2:98 ethyl ether/-petroleum ether. The material showed a single spot on thin layer chromatography (silica gel, 1:4 ethyl acetate/hexane) and the nuclear magnetic resonance and infrared spectra agreed with the assigned structure.

Anal. Calcd. for $C_{23}H_{34}O_2S$ (MW = 374.6) C, 73.74; H, 9.15; S, 8.56 Found: C, 73.64; H, 9.15; S, 8.51

EXAMPLE 3

1,2-Dihydro-2,2-dimethyl-9-hydroxy-7-(3-methyl-2-octyl)-4-oxo-4H-thieno-[2,3-c][1] benzopyran A. Diethyl 4,4-dimethyl-3-thiahexanedioate

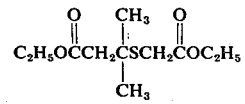

A mixture of 85 grams of ethyl dimethylacrylate, 88 g. of ethyl mercaptoacetate, 185 ml. of ethanol, and sodium ethoxide prepared from 1.6 g. of sodium, was refluxed 16 hrs., cooled and 500 ml. of ether was added. The reaction mixture was extracted with dilute aqueous sodium chloride and hydrochloric acid and then twice with aqueous sodium bicarbonate solution.

The reaction mixture was dried over magnesium sulfate and then distilled to give 128 g. of diethyl 4,4-dimethyl-3-thiahexanedioate, b.p. 90°–95°C./0.5 mm.

B. Ethyl 5,5-dimethyl-3-oxo-tetrahydrothiophene-2-carboxylate

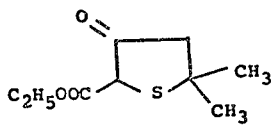

To a stirred suspension of 60 g. of potassium tertiary butoxide in 250 ml. of ether was added dropwise 100 g. of diethyl 4,4-dimethyl-3-thiahexanedioate in 100 ml. of ether over a one hour period while cooling in an ice bath. The mixture was stirred additionally one hour in the ice bath and then 35 g. of acetic acid and 150 ml. of water were added. The mixture was extracted with ether and dried over magnesium sulfate. By distillation 60.4 g. of product was obtained, b.p. 70°–75°C./0.5 mm.

C. 1,2-Dihydro-2,2-dimethyl-9-hydroxy-7-(3-methyl-2-octyl)-4-oxo-4H-thieno-[2,3-c][1] benzopyran

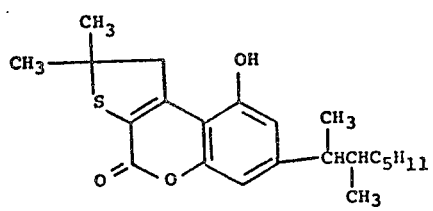

To 100 ml. of ethanol was added 6.2 g. of 5-(3-methyl-2-octyl)resorcinol and 6.2 g. of ethyl 5,5-dimethyl-3-oxotetrahydrothiophene-2-carboxylate. The mixture was cooled in ice and hydrogen chloride was bubbled in for one-half hour. The mixture was stoppered and held at room temperature for 3 days. It was then concentrated and ether added, extracted with water and then washed with dilute aqueous sodium bicarbonate solution. The etheral solution was dried over magnesium sulfate and concentrated. The product was crystallized from acetonitrile to give 5.0 g., m.p. 155°–163°C.

Anal. Calcd. for: $C_{22}H_{30}O_3S$ (MW=374.59) C, 70.56; H, 8.08; S, 8.54 Found: C, 70.06; H, 8.15; S, 8.87

EXAMPLE 4

1,2-Dihydro-9-hydroxy-7-(3-methyl-2-octyl)-2,2,4,4-tetramethyl4H-thieno-[2,3-c][1] benzopyran

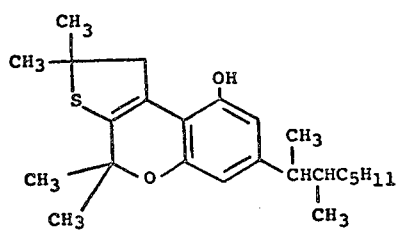

To a solution of methyl magnesium bromide (from 10 g. of Mg) in 150 ml. of ether was added 10 g. of 1,2-dihydro-2,2-dimethyl-9-hydroxy-7-(3-methyl-2-octyl)-4-oxo-4H-thieno-[2,3-c] [1] benzopyran in 100 ml. of benzene and 25 ml. of ether. The mixture was stirred overnight at 45°C. The reaction mixture was then treated with saturated ammonium chloride solution. The product was treated with 50 mg. of p-toluenesulfonic acid in 250 ml. of benzene and refluxed for 3 hours. The reaction mixture was shaken with sodium bicarbonate solution and dried over magnesium sulfate. The mixture was concentrated and chromatographed over activated magnesium silicate, eluting with 5% ethyl ether in petroleum ether. The product was obtained as 7.85 g. of a yellow oil.

Anal. Calcd. for: $C_{24}H_{36}O_2S$ (MW=388.61) C, 74.19; H, 9.34 Found: C, 73.94; H, 9.73

EXAMPLE 5

1,2-Dihydro-2,2-dimethyl-9-hydroxy-7-n-pentyl-4-oxo-4H-thieno-[2,3-c][1] benzopyran

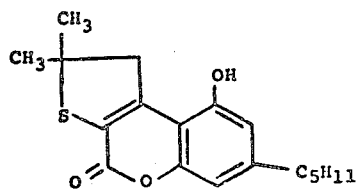

Ethyl 5,5-dimethyl-3-oxo-tetrahydrothiophene-2-carboxylate was reacted with 5-n-pentyl resorcinol following a procedure similar to that of Example 3-C to produce 1,2-dihydro-2,2-dimethyl-9-hydroxy-7-n-pentyl-4-oxo-4H-thieno-[2,3-c][1] benzopyran in a 72.5% yield, m.p. 203°–206°C.

Anal. Calcd. for: $C_{18}H_{22}O_3S$ (MW=318.44) C, 67.91; H, 6.97; S, 10.05 Found: C, 67.98; H, 7.06; S, 9.96

EXAMPLE 6

1,2-Dihydro-9-hydroxy-2,2,4,4-tetramethyl-7-n-pentyl-4Hthieno-[2,3-c][1] benzopyran

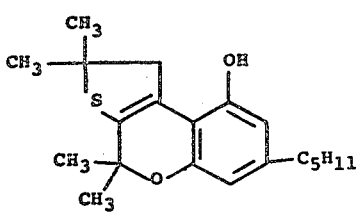

1,2-Dihydro-2,2-dimethyl-9-hydroxy-7-n-pentyl-4-oxo-4H-thieno-[2,3-c][1] benzopyran was reacted following a procedure similar to that in Example 4 to give a 79% yield of 1,2-dihydro-9-hydroxy-2,2,4,4-tetramethyl-7-n-pentyl-4H-thieno-[2,3-c][1] benzopyran, m.p. 109°–110°C. which was crystallized from petroleum ether.

Anal. Calcd. for: $C_{20}H_{28}O_2S$ (MW=332.44) C, 72.26; H, 8.49; S, 9.62 Found: C, 73.33; H, 8.82; S, 8.99

EXAMPLE 7

1,2-Dihydro-9-hydroxy-2-methyl-7-(3-methyl-2-octyl)-4-oxo4H-thieno-[2,3-c][1] benzopyran A. Diethyl 4-methyl-3-thiahexanedioate

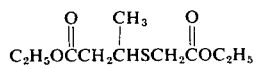

To 250 ml. of ethanol was added 2 g. of sodium followed by the addition of 117 g. of ethyl mercaptoacetate and then 100 g. of ethyl methylacrylate. The mixture was refluxed 17 hours, cooled and 500 ml. of ether added. The reaction mixture was extracted with water and then twice with aqueous sodium bicarbonate solution. The etheral solution was dried over magnesium sulfate and then distilled to give 139 g. of diethyl 4-methyl-3-thiahexanedioate, b.p. 90°–95°C/0.5 mm.

B. Ethyl 5-methyl-3-oxo-tetrahydrothiophene-2-carboxylate

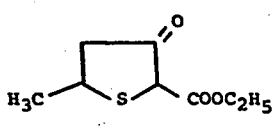

Diethyl 4-methyl-3-thiahexanedioate was converted to ethyl 5-methyl-3-oxo-tetrahydrothiophene-2-carboxylate following the general procedure of Example 3-B. The crude product (27 g.) had a boiling point of 70°–75°C./0.3 mm.

C. 1,2-Dihydro-9-hydroxy-2-methyl-7-(3-methyl-2-octyl)-4-oxo-4H-thieno-[2,3-c][1] benzopyran

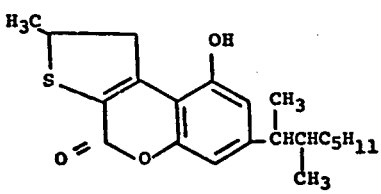

To 45 ml. of ethanol was added 8.8 g. of crude ethyl 5-methyl-3-oxo-tetrahydrothiophene-2-carboxylate and 5 g. of 5-(3-methyl-2-octyl) resorcinol. The mixture was cooled in ice and hydrogen chloride was bubbled in for onehalf hour. The mixture was stoppered and let stand at room temperature for 3 days. The reaction mixture was concentrated and dissolved in ether. The ether solution was extracted twice with water and once with aqueous sodium bicarbonate solution. The solution was dried over magnesium sulfate and concentrated. The product was crystallized from acetonitrile to give 4.65 g., m.p. 146°–149°C.

Anal. Calcd. for: $C_{21}H_{28}O_3S$ (MW=360.6) C, 69.97; H, 7.83 Found: C, 69.89; H, 8.03

EXAMPLE 8

1,2-Dihydro-2,4,4-trimethyl-9-hydroxy-7-(3-methyl-2-octyl)-4H-thieno-[2,3-c][1] benzopyran

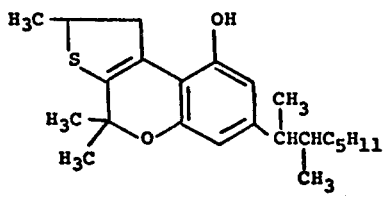

1,2-Dihydro-9-hydroxy-2-methyl-7-(3-methyl-2-octyl)-4-oxo-4H-thieno-[2,3-c][1] benzopyran is reacted in a manner similar to that set forth in Example 4 to give 1,2-dihydro-2,4,4-trimethyl-9-hydroxy-7-(3-methyl-2-octyl)-4H-thieno-[2,3-c][1] benzopyran in 81% yield as a yellow oil.

Anal. Calcd. for: $C_{23}H_{34}O_2S$ (MW=374.6) C, 73.76; H, 9.15; S, 8.54 Found: C, 74.09; H, 9.68; S, 8.25

EXAMPLE 9

1,2-Dihydro-9-hydroxy-2-methyl-7-n-pentyl-4-oxo-4H-thieno-[2,3-c][1] benzopyran

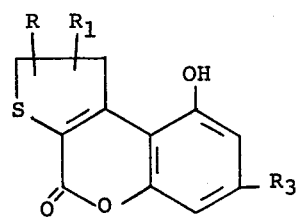

5-n-Pentyl resorcinol is reacted with methyl 5-methyl-3-oxo-tetrahydrothiophene-2-carboxylate to produce 1,2-dihydro-9-hydroxy-2-methyl-7-n-pentyl-4-oxo-4H-thieno[2,3-c][1] benzopyran, m.p. 188°–190°C, in 62% yield.

EXAMPLE 10

1,2-Dihydro-9-hydroxy-7-n-pentyl-2,4,4-trimethyl-4H-thieno-[2,3-c][1] benzopyran

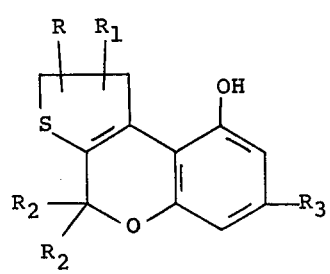

1,2-Dihydro-9-hydroxy-2-methyl-7-n-pentyl-4-oxo4H-thieno-[2,3-c][1] benzopyran is reacted as in Example 2 to give 1,2-dihydro-9-hydroxy-7-n-pentyl-2,4,4-trimethyl4H-thieno-[2,3-c][1] benzopyran.

The foregoing detailed description has been given for clearness of understanding only, and no unnecessary limitations should be understood therefrom, as modifications will be obvious to those skilled in the art.

What is claimed is:

1. A pharmaceutical composition in unit dosage form containing 2 to 300 mg. of a compound of the formulae and wherein R is lower alkyl having 1 to 5 carbons, $R_1$ is hydrogen or lower alkyl having 1 to 5 carbons, $R_2$ is lower alkyl and $R_3$ is alkyl having 1 to 20 carbon atoms, a phenyl-lower alkyl in which the phenyl is unsubstituted or is substituted with a lower-alkyl, lower-alkoxy, halo, nitro or lower-alkylmercapto group, or a cycloalkyl-lower alkyl group in which the cycloalkyl contains 3 to 8 carbons in the ring, and an inert pharmaceutically acceptable carrier.

2. The method of inducing analgesia in an animal which comprises administering to the animal a safe but effective amount of 1,2-dihydro-1,4,4-trimethyl-9-hydroxy-7-(3-methyl-2-octyl)-4H-thieno-[2,3-c][1]benzopyran or 1,2-dihydro-2,4,4-trimethyl-9-hydroxy-7-(3-methyl-2-octyl)-4H-thieno-[2,3-c][1] benzopyran to effect analgesia in the animal.

* * * * *

UNITED STATES PATENT AND TRADEMARK OFFICE
CERTIFICATE OF CORRECTION

PATENT NO. : 3,946,111
DATED : March 23, 1976
INVENTOR(S) : Martin Winn et al.

It is certified that error appears in the above-identified patent and that said Letters Patent are hereby corrected as shown below:

Column 1, last line, place a comma --,-- after "hexyl"; column 2, line 65, change "R$_3$4H" to --R$_3$-4H--; line 66, change "Thieno" to --thieno--; column 3, line 2, change "resorcinal" to --resorcinol--; line 6, change "ylporpyl" to --ylpropyl--; line 12, change "5R$_1$" to --5-R$_1$--; line 14, change "dimetnyl" to --dimethyl--; line 29, change "methyl4" to --methyl-4--; line 66, change "Formula 5" to --Formula 4--; column 4, line 13, change "thyl9" to --thyl-9--; line 29, insert a dash (-) before "9-"; column 6, line 1, change "methvl" to --methyl--; line 16, change "tetramechyl" to --tetramethyl--; line 54, change "SPA 38" to --SPA-38--; column 7, line 14, change "methyl2" to --methyl-2--; line 33, change "sedativehypnotic" to --sedative-hypnotic--; column 8, line 14, change "one of" to --one or--; line 54, change "oxo4H" to --oxo-4H--; column 11, line 37, change "oxotetra" to --oxo-tetra--; line 51, change "tetramethyl4H" to --tetramethyl-4H--; column 12, line 38, cahnge "4Hthieno" to --4H-thieno--; line 62, change "oxo4H" to --oxo-4H--; column 14, line 35, change "oxo4H" to --oxo-4H--; line 37, change "trimethyl4H" to --trimethyl-4H--.

Signed and Sealed this eighteenth Day of May 1976

[SEAL]

Attest:

RUTH C. MASON
Attesting Officer

C. MARSHALL DANN
Commissioner of Patents and Trademarks